US011802873B2

(12) United States Patent
Reinke et al.

(10) Patent No.: US 11,802,873 B2
(45) Date of Patent: Oct. 31, 2023

(54) CD8 T CELL SUBSETS AS A BIOMARKER FOR PREDICTING NON-FUSION AFTER SPINAL FUSION SURGERY

(71) Applicant: CHARITÉ UNIVERSITÄTSMEDIZIN BERLIN, Berlin (DE)

(72) Inventors: Simon Reinke, Berlin (DE); Sven Geissler, Berlin (DE); Georg Duda, Berlin (DE); Hans-Dieter Volk, Berlin (DE); Michael Fuchs, Berlin (DE); Katharina Schmidt-Bleek, Berlin (DE); Patrick Strube, Jena (DE); Matthias Pumberger, Berlin (DE)

(73) Assignee: CHARITÉ UNIVERSITÄTSMEDIZIN BERLIN, Berlin (DE)

( * ) Notice: Subject to any disclaimer, the term of this patent is extended or adjusted under 35 U.S.C. 154(b) by 748 days.

(21) Appl. No.: 16/618,118

(22) PCT Filed: May 29, 2018

(86) PCT No.: PCT/EP2018/064085
§ 371 (c)(1),
(2) Date: Nov. 28, 2019

(87) PCT Pub. No.: WO2018/219959
PCT Pub. Date: Dec. 6, 2018

(65) Prior Publication Data
US 2020/0182872 A1 Jun. 11, 2020

(30) Foreign Application Priority Data

May 29, 2017 (EP) ..................................... 17173320
Dec. 12, 2017 (EP) ..................................... 17206698

(51) Int. Cl.
| | | |
|---|---|---|
| G01N 33/53 | (2006.01) | |
| G01N 33/569 | (2006.01) | |
| C07K 14/51 | (2006.01) | |
| A61K 49/00 | (2006.01) | |
| A61K 38/00 | (2006.01) | |

(52) U.S. Cl.
CPC ... G01N 33/56972 (2013.01); A61K 49/0004 (2013.01); C07K 14/51 (2013.01); *A61K 38/00* (2013.01); *G01N 2333/70517* (2013.01); *G01N 2333/70521* (2013.01); *G01N 2333/70596* (2013.01); *G01N 2800/10* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,492,697 A | 2/1996 | Boyan et al. | |
| 2008/0019969 A1 | 1/2008 | Gorman | |
| 2015/0010924 A1* | 1/2015 | Duda | A61K 31/00 435/7.92 |

FOREIGN PATENT DOCUMENTS

EP 2623978 8/2013

OTHER PUBLICATIONS

Wallet et al., Increased inflammation but similar physical composition and function in older-aged, HIV-1 infected subjects, BMC Immunology, 2-15, 16:43, pp. 1-11. (Year: 2015).*
Van Der Vekiens et al., Human and equine cardiovascular endocrinology: beware to compare, Cardiovascular Endocrinology 2013, vol. 2, No. 4, pp. 67-76. (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Axelrad T W et al: "Bone morphogenetic proteins in orthopaedic surgery", Cytokine and Growth Factor Reviews, Elsevier LTD, GB, vol. 20, No. 5-6, Oct. 1, 2009, pp. 481-488.
S. Reinke et al: "Terminally Differentiated CD8+ T Cells Negatively Affect Bone Regeneration in Humans", Science Translational Medicine, vol. 5, No. 177, Mar. 20, 2013, p. 177ra36.
Werle Stephan et al: "Bone morphogenetic protein 7 and autologous bone graft in revision surgery for non-union after lumbar interbody fusion", Archives of Orthopaedic and Trauma Surgery, Springer Verlag, DE, vol. 136, No. 8, Jun. 20, 2016, pp. 1041-1049.

* cited by examiner

*Primary Examiner* — Gary Counts
(74) *Attorney, Agent, or Firm* — JMB Davis Ben-David (57) ABSTRACT

Provided herein is a method for predicting the probability of having or developing a non-fusion, wherein said method comprises determining the frequency of a subpopulation of CD8+ T cells selected from CD8+CD57+, CD8+CD28− and CD8+CD57+CD28− in a sample obtained from a patient. Also provided herein is a system for predicting the probability of having or developing a non-fusion.

7 Claims, 7 Drawing Sheets

CD8 T CELL SUBSETS AS A BIOMARKER FOR PREDICTING NON-FUSION AFTER SPINAL FUSION SURGERY

CROSS-REFERENCE TO RELATED APPLICATIONS

This is the U.S. National Stage of International Patent Application No. PCT/EP2018/064085 filed on May 29, 2018, which was published in English under PCT Article 21(2), and which in turn claims the benefit of European Patent Application Nos. 17173320.7 filed on May 29, 2017 and 17206698.7 filed Dec. 12, 2017.

The present invention relates to a method for predicting or detecting non-fusion, particularly before undergoing or after a spinal fusion surgery.

BACKGROUND

Chronic low back pain are one of the major reasons for disability or early work retirement in the industrial world. There are multiple reasons for the lower back pain (e.g. biological, anatomical, degeneration) resulting in serious problems like spondylisthesis, spondylosis, osteochondrosis or spinal stenosis. After an intensive long term conservative treatment with physiotherapy most of these affected patients have to undergo a spinal bone fusion surgery in terms of arthrodesis to relieve intractable pain.

Between 1998 and 2008, the annual number of spinal fusion surgeries in the US increased 2.4-fold (137%) from 174,223 to 413,171. [Rajaee S S et al.: *Spinal fusion in the United States: analysis of trends from 1998 to 2008*. 2012 Jan. 1; 37(1):67-76]. In 2011, 488,000 spinal fusion surgeries were reported in the United States of America, representing 3.1% ($6^{th}$ rank) all residential treatments. Moreover, with around 27,000$ per case, the surgical treatment of spinal fusion patient is most expensive[Agency for Healthcare Research and Quality (AHRQ)]. In Germany, a total of approx 230.000 spinal operations were conducted in 2011 representing an increase of 136% compared to 2008 [Deutsches Ärzteblatt]

Fusion rates following the surgical treatment for spinal fusion surgery shows a wide range of successful de novo bone formation from 46% to almost 100%. Based on the FDA guidelines, a delayed union is characterized "when healing has not advanced at the average rate for the location between 3-6 months". A non-fusion (pseudarthrosis) is defined by a "healing time of >9 month with no radiographic progression for 3 month." There are several factors that affect the success of fusion like patient co-morbidities, implant position and biologic deficiencies. Moreover, the various available bone graft materials can also affect the outcome of spinal fusion. Normally, the most used graft material comes from iliac crest bone.

However, assessing the patients function and quality of life, high rates of post-operative pain and morbidity often result from this additional procedure. Together with the abovementioned limited fusion rates due the biologic deficiencies of the patient this represents a serious medical problem with a high socio-economic impact. The usage of bone morphogenetic protein (BMP-2), is so far authorized in a revision scenario only, due to high costs and different side effects. Chun et al. reported in 2015: "The best treatment for pseudarthrosis is to prevent it from occurring after the initial operation". [Chun D S et al.; Lumbar pseudarthrosis: a review of current diagnosis and treatment. Neurosurg Focus. 2015 October; 39(4).]

Therefore, there is an unmet need for predicting the outcome after spinal fusion surgery to personalize as early as possible the therapeutic use of supporting growth factors, like BMP's, which are costly and not free of adverse effects.

It is therefore the objective of the present invention to provide means and methods for an accurate prediction or detection of non-fusion, particularly before or after a spinal fusion surgery.

DESCRIPTION OF THE INVENTION

The above objective is attained by a method having the features of claim 1 or 2 and by a system having the features of claim 7. Preferred embodiments are state in the sub claims and the description below.

According thereto, a first aspect of the invention relates to a method for predicting the probability of having or developing a non-fusion, particularly before undergoing a spinal fusion surgery or before revision surgery in failed spinal fusion or after a spinal fusion surgery. The method comprises determining the frequency of a subpopulation of CD8+ cells or CD8+CD3+CD45+ cells selected from CD8+CD57+, CD8+CD28− and CD8+CD57+CD28− in a sample obtained from a patient.

During the course of investigation of non-fusion after spinal fusion, it was surprisingly found that the spinal non-fusion was accompanied by a significantly elevated frequency of terminally differentiated CD8+ effector T cells expressing the phenotype CD45+CD3+CD8+CD28− or CD45+CD3+CD8+CD57+ or CD45+CD3+CD8+CD57+CD28− (CD8+ TEMRA). These cells are characterized by their tissue homing properties and strong bystander activity. They can be triggered independent on their T-cell receptor in an antigen-independent matter by cytokines delivered from cells of innate immunity (like macrophages or dendritic cells) triggered within the inflamed tissue as result of Toll Receptor (TLR). Damage-associated molecular pattern (DAMPs) interaction (e.g. IL-12, IL-18) can trigger the release of inflammatory cytokines (e.g. IFN-gamma) by these CD8+ TEMRA that support overwhelming inflammation and fibrosis. In contrast to other T cells, these CD8+ TEMRA do not need T-cell receptor (TCR)-crosslinking for activation.

If any cell population is designated "positive" with respect to a certain marker molecule herein, this designation shall particularly mean that said cell population can be stained by a common fluorescent-dye-labelled antibody against the marker molecule and will give a fluorescence signal of at least one, two or three log higher intensity compared to unlabeled cells or cells labelled with the same antibody but commonly known as not expressing said marker molecule or an isotype control antibody. Vice versa, any cell population that is designated "negative" with respect to certain marker molecule cannot be stained by a fluorescent-dye labelled antibody as described above against the marker molecule.

A second aspect of the invention relates to a method for monitoring the course of treatment of a non-fusion, particularly after spinal fusion surgery. The method comprises determining the frequency of a subpopulation of CD8+ T cells or CD8+CD3+CD45+ cells selected from CD8+CD57+, CD8+CD28− and CD8+CD57+CD28− in a sample obtained from said patient.

The term "non-fusion" or "nonunion" is used in its meaning known in the field of medicine, more particular in the field of orthopaedic surgery. It particularly refers to the absence of a consolidation of two bone segments within 9 months with no radiographic progression for 3 months, wherein particularly the two bone segments are naturally not connected by osseous tissue. Nonunion or non-fusion is also referred to as pseudoarthrosis.

Advantageously in case of revision surgery in failed spinal fusion, low doses of, e.g., BMP can be administered to a patient with a confirmed high risk of having or developing non-fusion.

In certain embodiments of the first or second aspect of the invention, the non-fusion is a non-fusion between two or more bones or bone segments naturally not connected by osseous tissue.

In certain embodiments of the first or second aspect of the invention, the non-fusion is a non-fusion between two or more vertebrae.

In certain embodiments of the first or second aspect of the invention, the sample is a blood sample, particularly a sample from the peripheral blood.

In certain embodiments of the first or second aspect of the invention, the sample is a sample that has been obtained from the patient before, during or after the spinal fusion surgery.

In certain embodiments of the first or second aspect of the invention, a sample exhibiting an at least 1.5 higher frequency of the subpopulation of CD8+ T cells or CD8+CD3+ CD45+ cells when compared to a standard value determined for a large population with normal fusion after spinal fusion surgery is assigned to a patient having an elevated probability for having or developing non-fusion after spinal fusion surgery.

In certain embodiments of the first or second aspect of the invention, a sample exhibiting an at least 1.8 higher frequency of the subpopulation of CD8+ T cells or CD8+CD3+ CD45+ cells when compared to a standard value determined for a large population with normal union after spinal fusion is assigned to a patient having an elevated probability for having or developing non-fusion after spinal fusion surgery.

In certain embodiments of the first or second aspect of the invention, a sample exhibiting an at least two-fold higher frequency of the subpopulation of CD8+ T cells or CD8+ CD3+CD45+ cells when compared to a standard value determined for a large population with normal union after spinal fusion is assigned to a patient having an elevated probability for having or developing non-fusion after spinal fusion surgery.

In certain embodiments of the first or second aspect of the invention, a sample exhibiting a fraction of CD8+CD57+ CD28− cells referred to the total sum of all CD8+ cell in the sample of at least 22.7% more particular of at least 33.1%, is assigned to a patient having an elevated probability for having or developing non-fusion after spinal fusion surgery.

In certain embodiments of the first or second aspect of the invention, a sample exhibiting a summed fraction of CD8+ CD57 cells and CD8+CD28− cells referred to the total sum of all CD8+ cells in the sample of at least 85.6% is assigned to a patient having an elevated probability for having or developing non-fusion after spinal fusion surgery.

In certain embodiments of the first or second aspect of the invention, a sample exhibiting a fraction of CD8+CD28− cells referred to the total sum of all CD8+ cells in the sample of at least 28.0%, more particular of at least 42.9%, is assigned to a patient having an elevated probability for having or developing non-fusion after spinal fusion surgery.

In certain embodiments of the first or second aspect of the invention, a sample exhibiting a fraction of CD8+CD57+ cells referred to the total sum of all CD8+ cells in the sample of at least 28.0%, more particular of at least 42.9%, is assigned to a patient having an elevated probability for having or developing non-fusion after spinal fusion.

In certain embodiments, the method according to the first or second aspect of the invention is performed by contacting a sample with a first ligand specifically reactive to a marker molecule selected from a marker group comprised of CD8 (UniProt P01732, P10966), CD28 (UniProt P10747) and CD57 (UniProt Q9P2W7), and determining the frequency of a cell presenting the marker molecule marked with the first ligand or determining the frequency of the first ligand bound to the marker molecule.

In certain embodiments of the first or second aspect of the invention, the first ligand is selected from the group comprised of an antibody, an antibody fragment, an antibody-like-molecule, an oligopeptide of 6 to 30 amino acids, and a nucleic acid aptamer molecule of 10 to 75 nucleotides in length, wherein the ligand is capable to bind to a member of the marker group described in the preceding paragraph with a dissociation constant of $10^{-8}$ mol/l or smaller.

In certain embodiments of the first or second aspect of the invention, the antibody fragment is the Fab domain of an antibody (the antigen binding region of an antibody) or a single chain antibody (scFv), a fusion protein consisting of the variable regions of light and heavy chains of an antibody connected by a peptide linker. An antibody fragment or an antibody-like molecule may be manufactured by suitable methods such as recombinant protein expression.

Such first ligand may also be developed by evolutive methods such as phage display, ribosome display or SELEX oligonucleotide selection, wherein polypeptides or oligonucleotides are selected according to their binding affinity to a target of interest. Additionally, higher affinity inhibitors may be identified by reiterative rounds of evolution and selection of the amino acid sequence or nucleotide sequence.

In certain embodiments of the first or second aspect of the invention, the oligopeptide of 6 to 30 amino acids as referred to above is a peptide derived from the part of a ligand, which is recognized by a member of the marker group described above.

In certain embodiments of the first or second aspect of the invention, the ligand that is recognized by a member of the marker group described above is selected from CD80 (Uniprot ID P33681) or CD86 (Uniprot ID P42081), which are ligands of CD28.

In certain embodiments of the first or second aspect of the invention, the first ligand is an antibody reactive to CD8, CD28, or CD57 and further comprises a fluorescent moiety for optical detection, wherein a marker molecule according to the preceding paragraphs is bound to such antibody, and cells presenting that marker molecule can be counted by a fluorescence based flow cytometric method such as fluorescence activated cell sorting.

In certain embodiments of the first or second aspect of the invention, the first ligand is specifically bound by a second ligand, wherein the second ligand comprises an enzymatic activity or a fluorescent moiety. A plurality of different marker molecules may be determined by use of a plurality of different first ligands, wherein each ligand specifically binds to a particular marker molecule.

In certain embodiments of the first or second aspect of the invention, each first ligand of the plurality comprises a certain enzymatic activity or fluorescent moiety as described above that can be spectroscopically distinguished form the enzymatic activity or fluorescent moiety of each other first ligand of the plurality.

In certain embodiments of the first or second aspect of the invention, each first ligand is bound be a specific second ligand having a certain enzymatic activity or fluorescent moiety that can be spectroscopically distinguished for the enzymatic activity or fluorescent moiety of each other second ligand.

In certain embodiments of the first or second aspect of the invention, the first and second ligand or pluralities thereof are antibodies and used in an Enzyme-linked immunosorbent assay.

In certain embodiments of the first or second aspect of the invention, the frequency of a subpopulation according to the preceding aspect of the invention, particularly of CD8+CD57+, CD8+CD28− or CD8+CD57+CD28− T cells, is determined by counting cells that are marked with a fluorescent antibody directed to a marker molecule selected from group comprised of CD8, CD28 and CD57 in a flow cytometric assay.

In certain embodiments of the first or second aspect of the invention, the antibodies according to the above aspects or embodiments of the invention are monoclonal antibodies of murine origin and comprise a fluorescent moiety for optical detection in the flow cytometry such as APC (allophycocyanin), FITC (fluorescein isothiocyanate) or PE (phycoerythrin).

In certain embodiments of the first or second aspect of the invention, the antibody is selected from the group comprised of APC-Cy7-labelled mouse anti-human CD8 IgG1, a murine monoclonal antibody conjugated with the tandem fluorophor APC-Cy7, FITC-labelled mouse anti-human CD57 IgM, a murine monoclonal antibody, and APC-H7 mouse anti-human CD28 IgG1, a murine monoclonal antibody conjugated with the tandem fluorophor APC-H7 being an analogue of APC-Cy7 and having the same spectroscopic properties.

According to another aspect of the invention, the use of a combination of antibodies for predicting the probability of having or developing a non-fusion, particularly after spinal fusion surgery is provided, wherein the combination comprises an anti-CD8-antibody and an anti-CD57-antibody, or an anti-CD8-antibody and an anti-CD28 antibody, or an anti-CD8-antibody, an anti-CD28-antibody and an anti-CD57-antibody, and wherein said antibodies are suitable for fluorescence based flow cytometry.

In certain embodiments of above aspect of the invention, the antibodies according to the above aspect of the invention are monoclonal antibodies of murine origin and comprise a fluorescent moiety for optical detection in the flow cytometry such as APC (allophycocyanin), FITC (fluorescein isothiocyanate) or PE (phycoerythrin).

In certain embodiments of the above aspect of the invention, the antibody is selected from the group comprised of APC-Cy7-labelled mouse anti-human CD8 IgG1, a murine monoclonal antibody conjugated with the tandem fluorophor APC-Cy7, FITC-labelled mouse anti-human CD57 IgM, a murine monoclonal antibody, and APC-H7 mouse anti-human CD28 IgG1, a murine monoclonal antibody conjugated with the tandem fluorophor APC-H7 being an analogue of APC-Cy7 and having the same spectroscopic properties.

According to a further aspect of the invention, a system for predicting the probability of having or developing non-fusion, particularly before undergoing a spinal fusion surgery, or for monitoring the course of treatment of non-fusion, particularly after spinal fusion surgery, of a patient is provided, comprising
 a device for determination the frequency of a cell population in a sample from a patient, and
 a programmed microprocessor,
wherein the programmed microprocessor is configured to run a method according to the above aspects or embodiments of the invention.

In certain embodiments, the device is a flow cytometer, comprising a flow cell for transporting and aligning cells, a light source such as a laser and a detector suitable for measuring light or other biophysical parameters such as impedance. Such device may be used for determining the frequency of subpopulations of CD8+ cells according to the above aspects and embodiments of the invention.

In certain embodiments, the device is spectrophotometer or a plate reader, comprising a compartment holding the sample such as a cuvette or a microtiter plate, a light source and a UV/Vis detector suitable for measurement of absorbance or fluorescence, such as a diode array.

In certain embodiments, the programmed microprocessor is integrated in the device described in the preceding paragraphs or is part of a control unit or a computer for operating the device.

In certain embodiments, the device described above is configured to determine the frequency of the subpopulation of CD8+ T cells or CD8+CD3+CD45+ cells according to the above aspects and embodiments of the invention, particularly of CD8+CD57+, CD8+CD28− or CD8+CD57+CD28− T cells.

According to yet another aspect of the invention, a bone morphogenetic protein for use in a method for preventing or treating non-fusion after spinal fusion surgery is provided, wherein the bone morphogenetic protein is administered during or after undergoing a spinal fusion surgery to a patient that has an elevated probability of developing or having a non-fusion after spinal bone fusion surgery.

In certain embodiments, the bone morphogenetic protein is BMP2 or BMP7.

In certain embodiments, the elevated probability of developing or having a non-fusion after spinal bone fusion surgery have been determined by a method according to the first aspect or any embodiment thereof.

EXAMPLES

Figure 1:
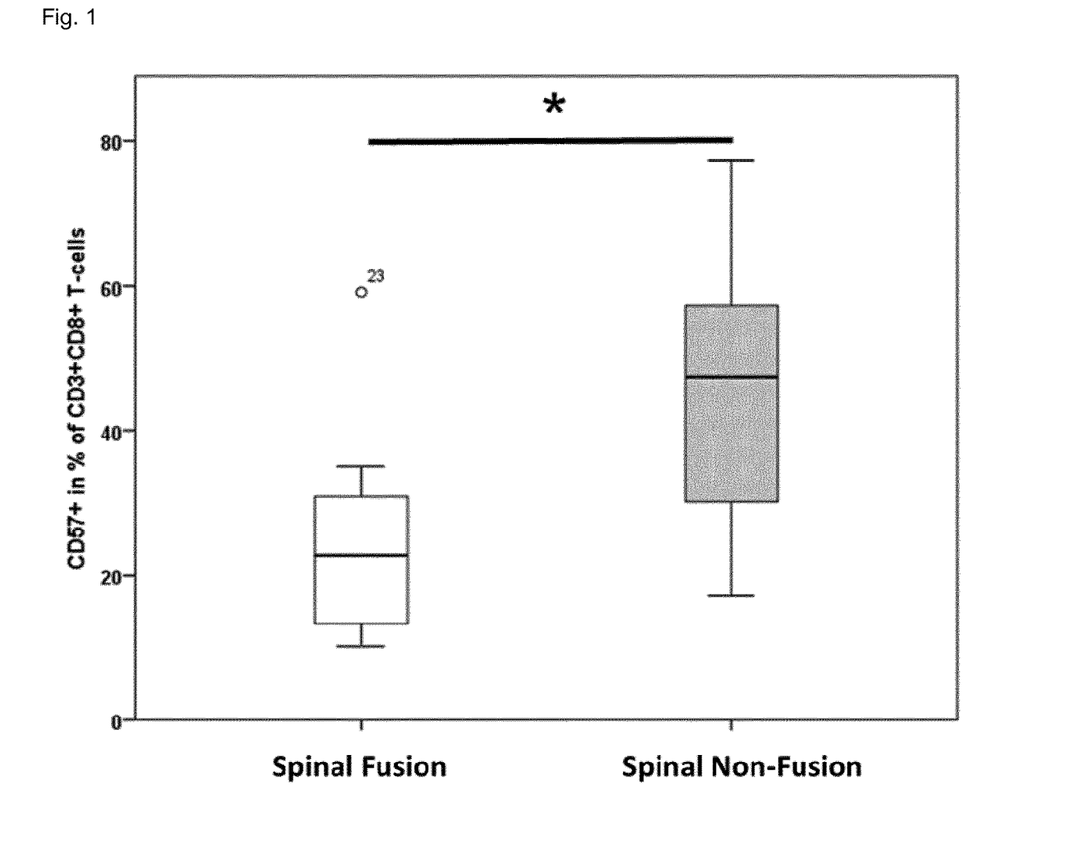
FIG. 1 shows the results of flow cytometric analyses of the circulating immune cell subset CD45+CD3+CD8+CD57+ T cells in the peripheral blood of patients with spinal non-fusion and normal fusion. Spinal non-fusion patients (healing class 2) showed a significantly higher frequency of CD45+CD3+CD8+CD57+ T cells (CD57+ in % of CD45+CD3+CD8+ T cells) compared to normal healing patients (healing class 1) indicates a dramatic increase of terminally differentiated CD8+ effector cells (TEMRA CD8+). *=P<0.001; Mann-Whitney U test.
Figure 2:
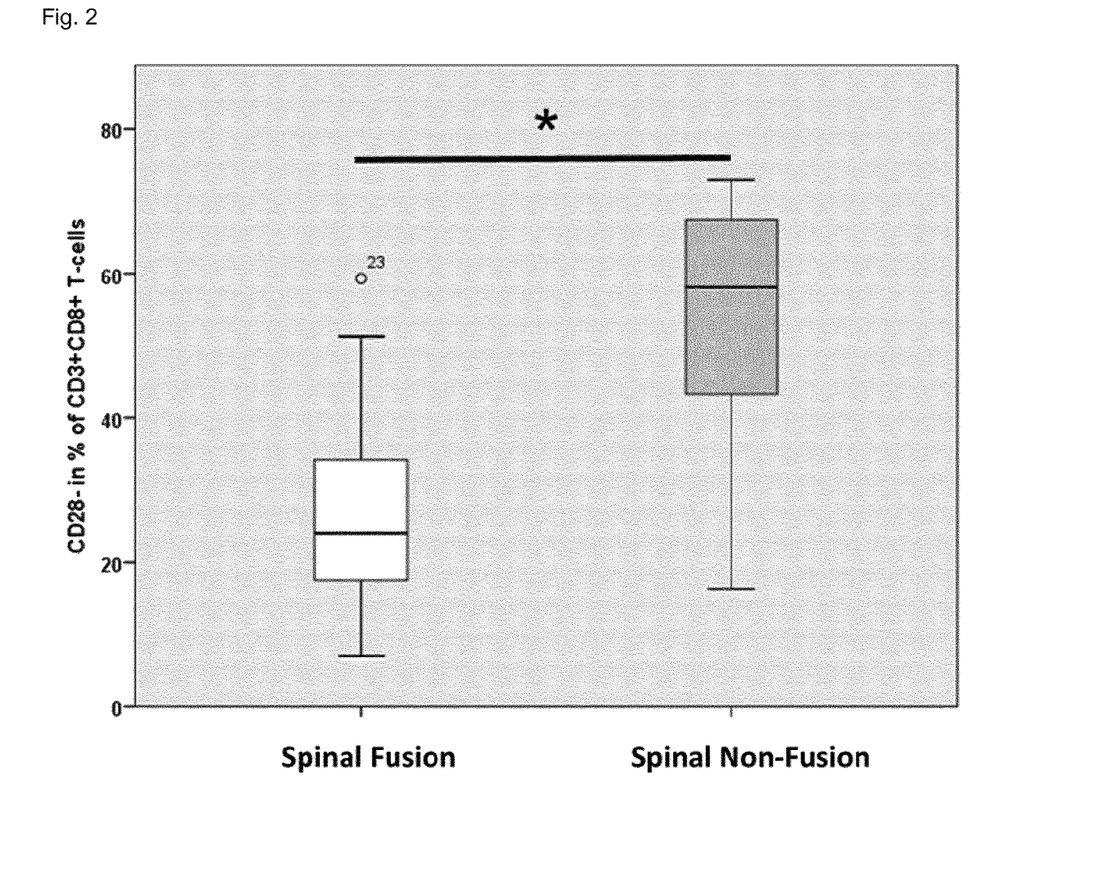
FIG. 2 Results of flow cytometric analyses of the circulating immune cell subset CD45+CD3+CD8+CD28− T cells in the peripheral blood of patients with spinal non-fusion and normal fusion. Spinal non-fusion patients (healing class 2) showed a significantly higher frequency of CD45+CD3+CD8+CD28− T cells (CD28− in % of CD45+CD3+CD8+ T cells) compared to normal healing patients (healing class 1) indicates a dramatic increase of terminally differentiated CD8+ effector cells (TEMRA CD8+). *=P<0.001; Mann-Whitney U test.
Figure 3:
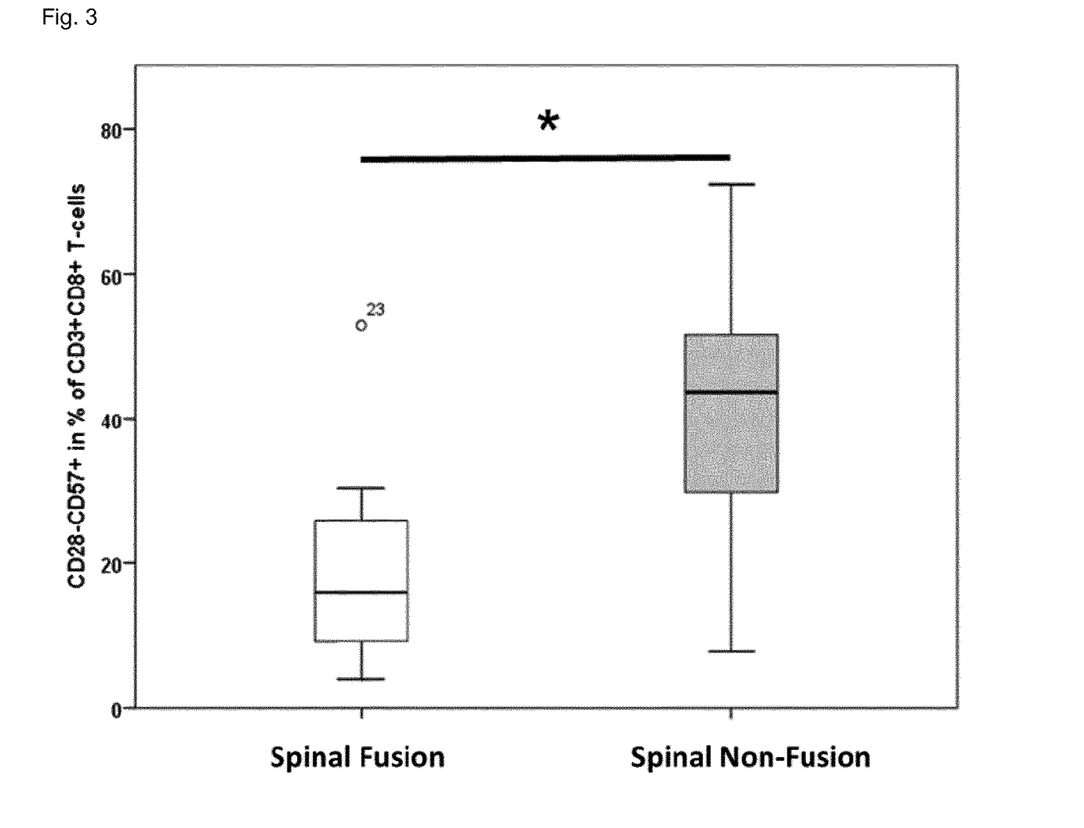
FIG. 3 shows the results of flow cytometric analyses of the circulating immune cell subset CD45+CD3+CD8+CD57+28− T cells in the peripheral blood of patients with spinal non-fusion and normal fusion. Spinal non-fusion patients (healing class 2) showed a significantly higher frequency of CD45+CD3+CD8+CD57+28− T cells (CD57CD28−+ in % of CD45+CD3+CD8+ T cells) compared to normal healing patients (healing class 1) indicates a dramatic increase of terminally differentiated CD8+ effector cells (TEMRA CD8+). *=P<0.001; Mann-Whitney U test.
Figure 4:
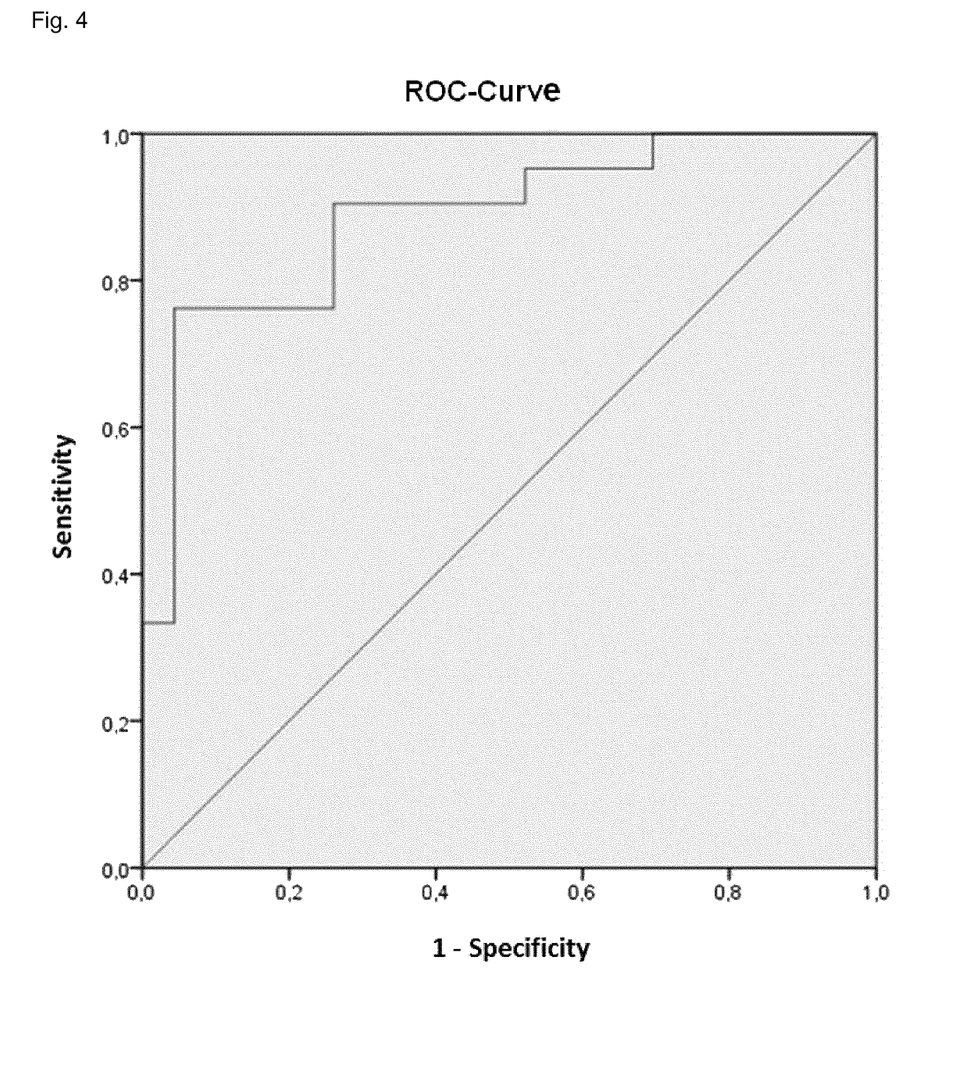
FIG. 4 illustrates the receiver operating characteristics (ROC) based on the summation of the expression of CD57+ in % of CD45+CD3+CD8+ T cells and CD28− in % of CD45+CD3+CD8+ T cells. The ROC analysis showed a high sensitivity (76%) as well as specificity (96%) in the detection of the affected patients based on their blood levels using a cut-off level of 85.6% with an area under the curve (AUC): 0.886 and p<0.001.
Figure 5:
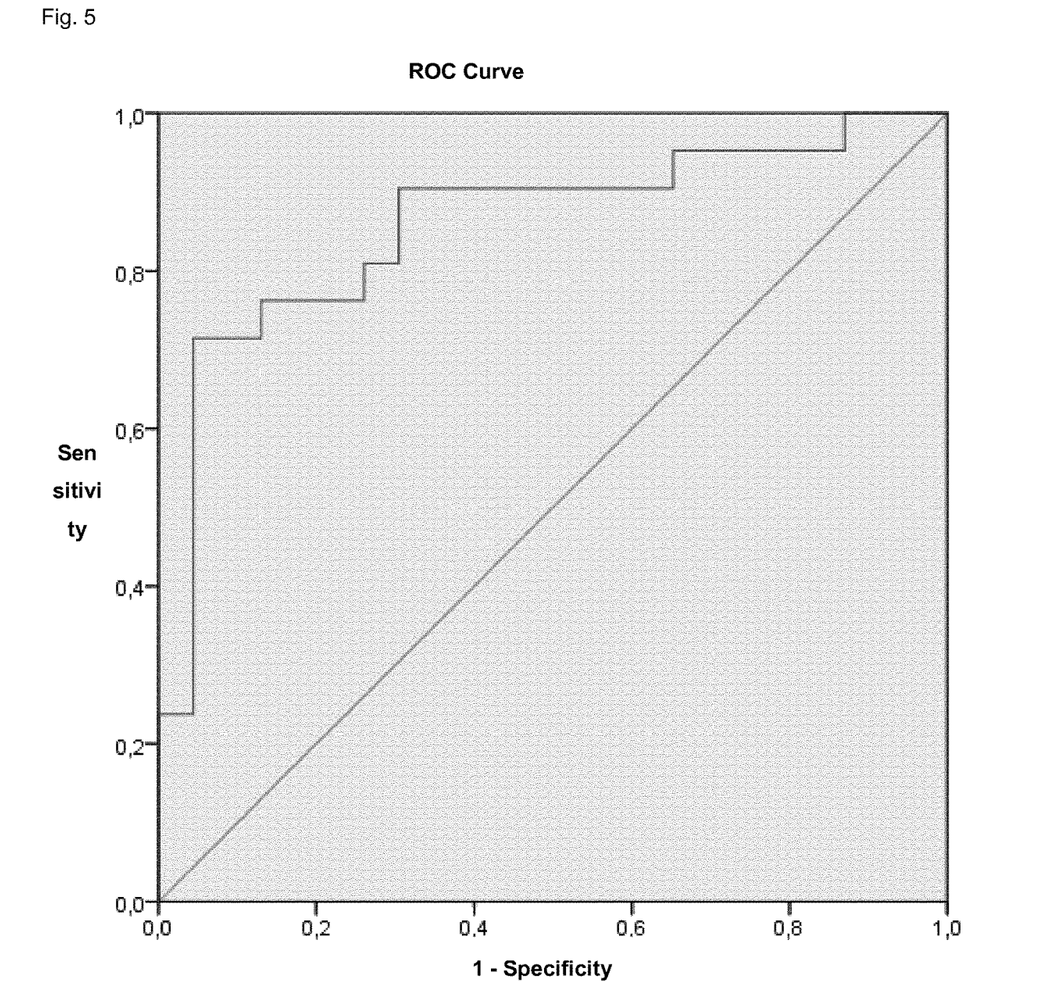
FIG. 5 illustrates the receiver operating characteristic (ROC) based on the expression of CD57+CD28− in % of CD45+CD3+CD8+ T cells with an area under the curve (AUC): 0.859 and p<0.001. The ROC analysis showed a high sensitivity (90%) as well as a specificity (71%) in the detection of the affected patients based on their blood levels using a cut-off level of 22.7%. A cut-off level of 33.1% showed a sensitivity of 71% with a higher specificity (96%)
Figure 6:
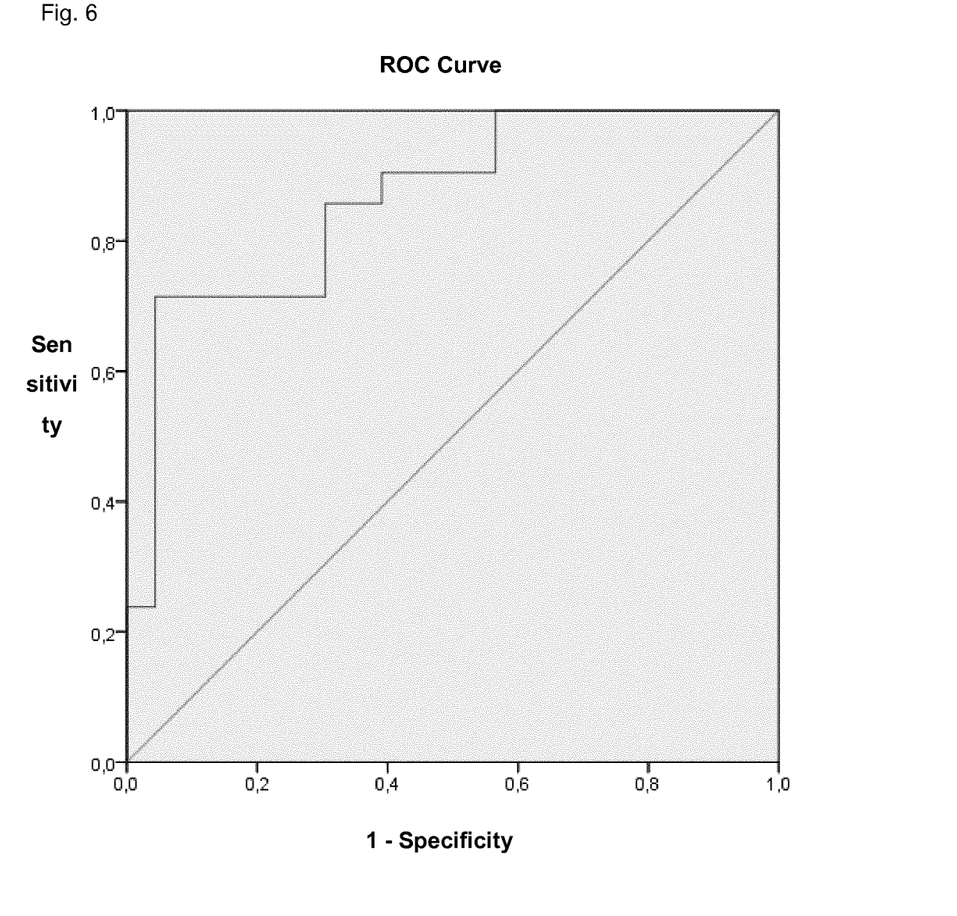
FIG. 6 illustrates the receiver operating characteristics (ROC) based on the expression of CD57+ in % of CD45+CD3+CD8+ T cells with an area under the curve (AUC): 0.863 and p<0.001. The ROC analysis showed a high sensitivity (90%) as well as a specificity (61%) in the detection of the affected patients based on their blood levels using a cut-off level of 24.4%. A cut-off level of 37.6% showed a sensitivity of 71% with a higher specificity (96%)
Figure 7:
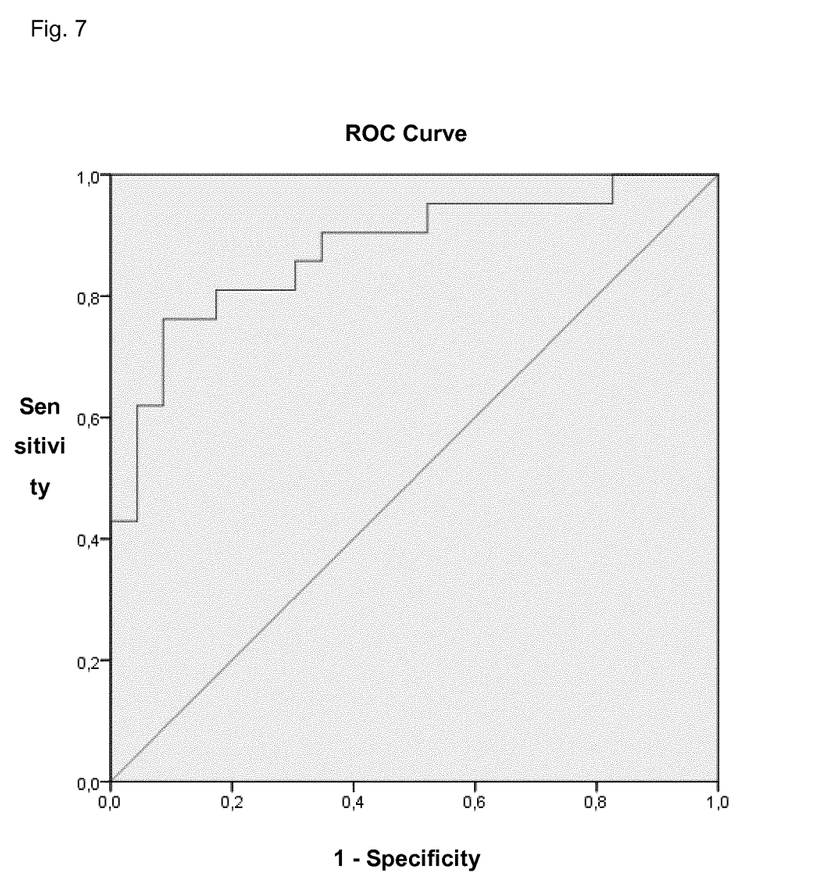
FIG. 7 illustrates the receiver operating characteristics (ROC) based on the expression of CD28− in % of CD45+CD3+CD8+ T cells with an area under the curve (AUC): 0.876 and p<0.001. The ROC analysis showed a high sensitivity (90%) as well as a specificity (66%) in the detection of the affected patients based on their blood levels using a cut-off level of 28.0%. A cut-off level of 42.9% showed a sensitivity of 76% with a higher specificity (91%)

In order to define novel biomarkers for predicting the individual risk and to identify novel therapeutic targets, the inventors included 44 patients that received a spinal bone fusion surgery with secured vertebral body fusion results into a retrospective study. These patients were classified in patients with normal vertebral body fusion (n=23) and patients with pseudarthrosis/non-fusion (n=21), based on their CT-scan results.

Table 1 shows the characterization and blood parameters of the patients involved in the retrospective study (spinal fusion and spinal non-fusion patients)

| Parameter | Spinal non-fusion (n = 21) | Spinal fusion (n = 23) | p-value |
| --- | --- | --- | --- |
| Age (y) | 70.7 ± 8.1 | 63.7 ± 10.1 | 0.01 |
| Sex | 6 male/ 15 female (28.6%)/ (71.4%) | 10 male/ 13 female (43.5%)/ (56.5%) | 0.3 |
| Time to revision or revision free (month) | 21.7 ± 12.7 Minimum: 8 Maximum: 47 | 27.0 ± 10.3 Minimum: 12 Maximum: 57 | 0.1 |
| Height (m) | 1.62 ± 0.1 | 1.66 ± 0.1 | 0.3 |
| Weight (kg) | 76.9 ± 10.7 | 79.6 ± 13.7 | 0.5 |
| BMI | 29.1 ± 3.2 | 29.3 ± 6.4 | 0.9 |
| Leucocytes (/nL) | 8.5 ± 3.9 | 6.7 ± 2.0 | 0.06 |
| Haemoglobin (g/L) | 13.2 ± 1.9 | 14.2 ± 1.3 | 0.06 |
| Haematocrite (%) | 0.39 ± 0.05 | 0.41 ± 0.03 | 0.07 |
| Erythrocytes (/pL) | 4.4 ± 0.6 | 4.6 ± 0.5 | 0.2 |
| Thrombocytes (/nL) | 271.5 ± 77.8 | 253.0 ± 53.0 | 0.3 |
| Sodium (mmol/L) | 139.0 ± 3.9 | 139.0 ± 2.9 | 0.9 |
| Potassium (mmol/L) | 4.2 ± 0.4 | 4.1 ± 0.3 | 0.6 |
| Calcium (mmol/L) | 2.4 ± 0.1 | 2.3 ± 0.1 | 0.4 |
| Glucose (mg/dL) | 102.3 ± 24.1 | 109.1 ± 41.8 | 0.5 |
| Creatinin (mg/dL) | 0.88 ± 0.2 | 0.81 ± 0.2 | 0.3 |
| Urea (mg/dL) | 32.8 ± 9.2 | 32.4 ± 11.3 | 0.9 |
| Albumin (g/L) | 42.9 ± 9.3 | 44.5 ± 2.7 | 0.4 |
| GPT (U/L) | 24.5 ± 19.9 | 28.4 ± 16.0 | 0.5 |
| GOT (U/L) | 26.5 ± 14.2 | 31.0 ± 28.8 | 0.5 |
| CRP (mg/L) | 0.9 ± 1.1 | 4.0 ± 6.0 | 0.03 |

Table 2: shows the blood parameters and time to diagnosis of spinal non-fusion at the initial and revision surgery for non-fusion patients.

| Parameter | Spinal non-fusion Initial Surgery | Spinal non-fusion Revision Surgery | p-value |
| --- | --- | --- | --- |
| Time to diagnose non-fusion (month) | | 8 month = n = 2 = 9.5% 10 month = n = 2 = 9.5% 11 month = n = 2 = 9.5% 12 month = n = 3 = 14.3% 13 month = n = 1 = 4.8% 18 month = n = 1 = 4.8% 19 month = n = 1 = 4.8% 24 month = n = 1 = 4.8% 26 month = n = 1 = 4.8% 31 month = n = 1 = 4.8% 33 month = n = 1 = 4.8% 36 month = n = 2 = 9.5% 40 month = n = 2 = 9.5% 47 month = n = 1 = 4.8% | |
| Revision performed | — | 15/21 (71.4%) | — |
| Spongiosa + BMP-2 | — | 8/15(53.3%) | — |
| Spongiosa | | 7/15 (46.7%) | — |
| Leucocytes (/nL) | 8.5 ± 3.9 | 6.5 ± 1.6 | 0.9 |
| Haemoglobin (g/L) | 13.2 ± 1.9 | 13.9 ± 1.9 | 0.6 |
| Haematocrite (%) | 0.39 ± 0.05 | 0.41 ± 0.06 | 0.8 |
| Erythrocytes (/pL) | 4.4 ± 0.6 | 4.4 ± 0.7 | 0.7 |
| Thrombocytes (/nL) | 271.5 ± 77.8 | 261.4 ± 68.1 | 0.5 |
| Sodium (mmol/L) | 139.0 ± 3.9 | 137.7 ± 4.4 | 0.4 |
| Potassium (mmol/L) | 4.2 ± 0.4 | 4.2 ± 0.4 | 0.7 |
| Calcium (mmol/L) | 2.4 ± 0.1 | 2.4 ± 0.1 | 0.5 |
| Glucose (mg/dL) | 102.3 ± 24.1 | 106.4 ± 23.8 | 0.3 |
| Creatinin (mg/dL) | 0.88 ± 0.2 | 0.87 ± 0.2 | 0.7 |
| Urea (mg/dL) | 32.8 ± 9.2 | 36.5 ± 9.1 | 0.3 |
| Albumin (g/L) | 42.9 ± 9.3 | 43.8 ± 2.9 | 0.4 |
| GPT (U/L) | 24.5 ± 19.9 | 19.6 ± 9.7 | 0.2 |
| GOT (U/L) | 26.5 ± 14.2 | 22.7 ± 4.9 | 0.2 |
| CRP (mg/L) | 0.9 ± 1.1 | 4.4 ± 9.5 | 0.01 |

As established in literature and routinely used in clinics, there are time dependent and radiological criteria for the classification of a non-fusion. To fulfil the definition of a non-fusion process, the patients have to meet one or more of the following criteria.

Time Dependent Criteria:

An incomplete vertebral body fusion after at least 24 post-operative weeks based on the presence of scar tissue formation in the intervertebral zone. (Zenya Ito et al., SPINE Volume 35, Number 21, pp E1101-E1105; 2010)

Radiological+Clinical Criteria:
1) no bridging of the trabecular bone connecting the two vertebral bodies,
2) angular motion in excess of 5 degrees
3) sagittal translation in excess of 3 mm 4) radiolucencies that involve more than half of the interfaces between the dowels and the host vertebral end plates Based on this former classification, the non-fusion patients showed differences in immune and inflammatory parameters in peripheral blood. Particularly, the spinal non-fusion was strongly associated with a significantly enhanced frequency (>2 fold) of terminally differentiated CD8+ effector T cells expressing the phenotype CD45+CD3+CD8+ CD28− and/or CD45+CD3+CD8+CD57+(CD8+ TEMRA).

Accordingly, patients with enhanced levels of CD8+ TEMRA cells, because of a personal history of chronic immunostimulation (e.g. by persistent and frequently reactivating viruses like CMV/EBV), have a worse vertebral body fusion or quality following spinal fusion surgery as a result of an overwhelming inflammation that inhibits normal vertebral body fusion.

The data presented herein demonstrate that the individual immune profile (frequency of CD8+ TEMRA) is a reliable biomarker for predicting impaired bone fusion patients allowing early interventions with known and established methods.

The invention claimed is:

1. A method for treating a human patient that has an elevated probability of having or developing a non-fusion before undergoing a spinal fusion surgery or after a spinal fusion surgery, wherein said method comprises detecting the frequency of a subpopulation of CD8+ T cells selected from the group consisting of CD8+CD57+, CD8+CD28− and CD8+CD57+CD28− in a blood sample obtained from a human patient, thereby determining if the human patient has an elevated probability for having or developing non-fusion, wherein:
    a blood sample exhibiting an at least two-fold higher frequency of said subpopulation of CD8+ T cell when compared to a standard value determined for a population with normal fusion after bone fusion is assigned to a human patient having an elevated probability for having or developing non-fusion after spinal fusion surgery, and/or
    a blood sample exhibiting a fraction of CD8+CD57+ CD28− cells referred to the total sum of all CD8+ cell in said blood sample of at least 22.7% is assigned to a human patient having an elevated probability for having or developing non-fusion after spinal fusion surgery, and/or
    a blood sample exhibiting a summed fraction of CD8+ CD57+ cells and CD8+CD28− cells referred to the total sum of all CD8+ cells in said blood sample of at least 85.6% is assigned to a human patient having an elevated probability for having or developing non-fusion after spinal fusion surgery, and/or
    a blood sample exhibiting a fraction of CD8+CD57+ cells referred to the total sum of all CD8+ cells in said blood sample of at least 24.4% is assigned to a human patient having an elevated probability for having or developing non-fusion after spinal fusion surgery, and/or
    a blood sample exhibiting a fraction of CD8+CD28− cells referred to the total sum of all CD8+ cells in said blood sample of at least 28.0% is assigned to a human patient having an elevated probability for having or developing non-fusion after spinal fusion; and
administering to the human patient determined to have an elevated probability for having or developing non-fusion after spinal fusion, a bone morphogenic protein selected from the group consisting of BMP-2 and BMP-7.

2. The method according to claim 1, wherein said non-fusion is a non-fusion between two or more bones or bone segments naturally not connected by osseous tissue.

3. The method according to claim 1, wherein said blood sample is a blood sample that has been obtained before, during or after spinal fusion surgery from said human patient.

4. The method according to claim 1, wherein a blood sample exhibiting a fraction of CD8+CD57+CD28− cells referred to the total sum of all CD8+ cell in said blood sample of at least 33.1%, is assigned to a human patient having an elevated probability for having or developing non-fusion after spinal fusion surgery.

5. The method according to claim 1, wherein a blood sample exhibiting a fraction of CD8+CD57+ cells referred to the total sum of all CD8+ cells in said blood sample of at least 37.6%, is assigned to a human patient having an elevated probability for having or developing non-fusion after spinal fusion surgery.

6. The method according to claim 1, wherein a blood sample exhibiting a fraction of CD8+CD28− cells referred to the total sum of all CD8+ cells in said blood sample of at least 42.9%, is assigned to a human patient having an elevated probability for having or developing non-fusion after spinal fusion.

7. The method according to claim 1, wherein said non-fusion is a non-fusion between two or more vertebrae.

* * * * *